(12) United States Patent
Barak et al.

(10) Patent No.: US 9,618,621 B2
(45) Date of Patent: Apr. 11, 2017

(54) COMPACT OPTICAL TRACKER HAVING AT LEAST ONE VISUAL INDICATOR COUPLED TO EACH OF OPTICAL TRACKER SENSORS

(71) Applicant: Elbit Systems Ltd., Haifa (IL)

(72) Inventors: Lior Barak, Binyamina (IL); Ron Kornblit, Haifa (IL); Rani Ben-Yishai, Tel-Aviv (IL)

(73) Assignee: Elbit Systems Ltd., Haifa (IL)

( * ) Notice: Subject to any disclaimer, the term of this patent is extended or adjusted under 35 U.S.C. 154(b) by 50 days.

(21) Appl. No.: 14/547,542

(22) Filed: Nov. 19, 2014

(65) Prior Publication Data

US 2015/0136947 A1 May 21, 2015

(30) Foreign Application Priority Data

Nov. 21, 2013 (IL) .......................................... 229563

(51) Int. Cl.
*G01S 17/66* (2006.01)
*G01S 17/02* (2006.01)

(52) U.S. Cl.
CPC ............ *G01S 17/66* (2013.01); *G01S 17/023* (2013.01)

(58) Field of Classification Search
CPC . G01S 17/023; G01S 17/66; G08B 13/19602; G08B 13/19608
USPC ................................... 250/221, 208.1, 214 R
See application file for complete search history.

(56) References Cited

U.S. PATENT DOCUMENTS

| | | | |
|---|---|---|---|
| 5,734,736 A | 3/1998 | Palmer et al. | |
| 6,128,003 A | 10/2000 | Smith et al. | |
| 9,007,432 B2* | 4/2015 | Chuang | G08B 13/19619 348/39 |
| 2005/0163346 A1 | 7/2005 | Van den Bergen et al. | |
| 2008/0144880 A1 | 6/2008 | DeLuca | |
| 2009/0209343 A1 | 8/2009 | Foxlin et al. | |

(Continued)

FOREIGN PATENT DOCUMENTS

| | | |
|---|---|---|
| WO | WO-2009/040792 | 4/2009 |
| WO | WO 2011/128766 | 10/2011 |
| WO | WO 2012/125557 | 9/2012 |

OTHER PUBLICATIONS

International Search Report for International Application No. PCT/IL2014/051010 mailed Mar. 29, 2015.

*Primary Examiner* — Que T Le
(74) *Attorney, Agent, or Firm* — Pearl Cohen Zedek Latzer Baratz LLP (57) ABSTRACT

An optical tracker is provided herein. The tracker may include at least two optical tracker sensors, facing at least partially each other. Each optical tracker sensor may include: a pixel array sensor configured to generate a pixel-by-pixel stream of values representing a scene; at least one visual indicator physically coupled to said pixel array sensor; and an integrated circuit (IC) physically coupled to said at least one pixel array sensor, and configured to: receive said pixel-by-pixel stream of values; and apply a binary large object (BLOB) analysis to said stream, to yield BLOB parameters indicative of the at least one visual indicator present in the scene in a single pass of the pixels representing the scene; and a computer processor configured to receive said BLOB parameters and calculate a relative position and/or orientation, or a partial data thereof, of the at least two optical tracker sensors.

19 Claims, 5 Drawing Sheets

(56) References Cited

U.S. PATENT DOCUMENTS

2011/0080490 A1     4/2011    Clarkson et al.
2011/0128372 A1     6/2011    Malecki et al.
2012/0262558 A1    10/2012    Boger et al.
2013/0002855 A1     1/2013    Ratti
2013/0182077 A1     7/2013    Holz \* cited by examiner

COMPACT OPTICAL TRACKER HAVING AT LEAST ONE VISUAL INDICATOR COUPLED TO EACH OF OPTICAL TRACKER SENSORS

CROSS REFERENCE TO RELATED APPLICATIONS

This application claims the benefit of Israeli Patent Application No. 229563 filed on Nov. 21, 2013, which is incorporated herein by reference in its entirety.

FIELD OF THE INVENTION

The present invention relates generally to the field of optical trackers and more particularly, to local tracking data extraction for facilitating data transmission.

BACKGROUND OF THE INVENTION

Tracking objects using video cameras requires both bandwidth and computational power that inevitably lead to latency issues. In some applications it is desirable to be able to track objects quickly without the need for high computational power or a high bandwidth of the communication link between the tracking device and the control module.

SUMMARY OF THE INVENTION

According to some embodiments of the present invention, an optical tracker is provided herein. The tracker may include at least two optical tracker sensors, facing at least partially each other. Each optical tracker sensor may include: at least one pixel array sensor configured to generate a stream of pixel values representing a scene; at least one visual indicator physically coupled to said at least one pixel array sensor; and an integrated circuit (IC) physically coupled to said at least one pixel array sensor, and configured to: receive said stream of pixel values; and apply a binary large object (BLOB) analysis to said stream, to yield BLOB parameters indicative of the at least one visual indicator present in the scene in a single pass of the pixels representing the scene; and a computer processor configured to receive said BLOB parameters and calculate a relative position and/or orientation, or a partial data thereof, of the at least two optical tracker sensors.

These additional, and/or other aspects and/or advantages of the present invention are set forth in the detailed description which follows.

BRIEF DESCRIPTION OF THE DRAWINGS

For a better understanding of the invention and in order to show how it may be implemented, references are made, purely by way of example, to the accompanying drawings in which like numerals designate corresponding elements or sections. In the accompanying drawings.

The drawings together with the following detailed description make the embodiments of the invention apparent to those skilled in the art.

DETAILED DESCRIPTION OF THE INVENTION

With specific reference now to the drawings in detail, it is stressed that the particulars shown are for the purpose of example and solely for discussing the preferred embodiments of the present invention, and are presented in the cause of providing what is believed to be the most useful and readily understood description of the principles and conceptual aspects of the invention. In this regard, no attempt is made to show structural details of the invention in more detail than is necessary for a fundamental understanding of the invention. The description taken with the drawings makes apparent to those skilled in the art how the several forms of the invention may be embodied in practice.

Before explaining the embodiments of the invention in detail, it is to be understood that the invention is not limited in its application to the details of construction and the arrangement of the components set forth in the following descriptions or illustrated in the drawings. The invention is applicable to other embodiments and may be practiced or carried out in various ways. Also, it is to be understood that the phraseology and terminology employed herein is for the purpose of description and should not be regarded as limiting.

Figure 1:
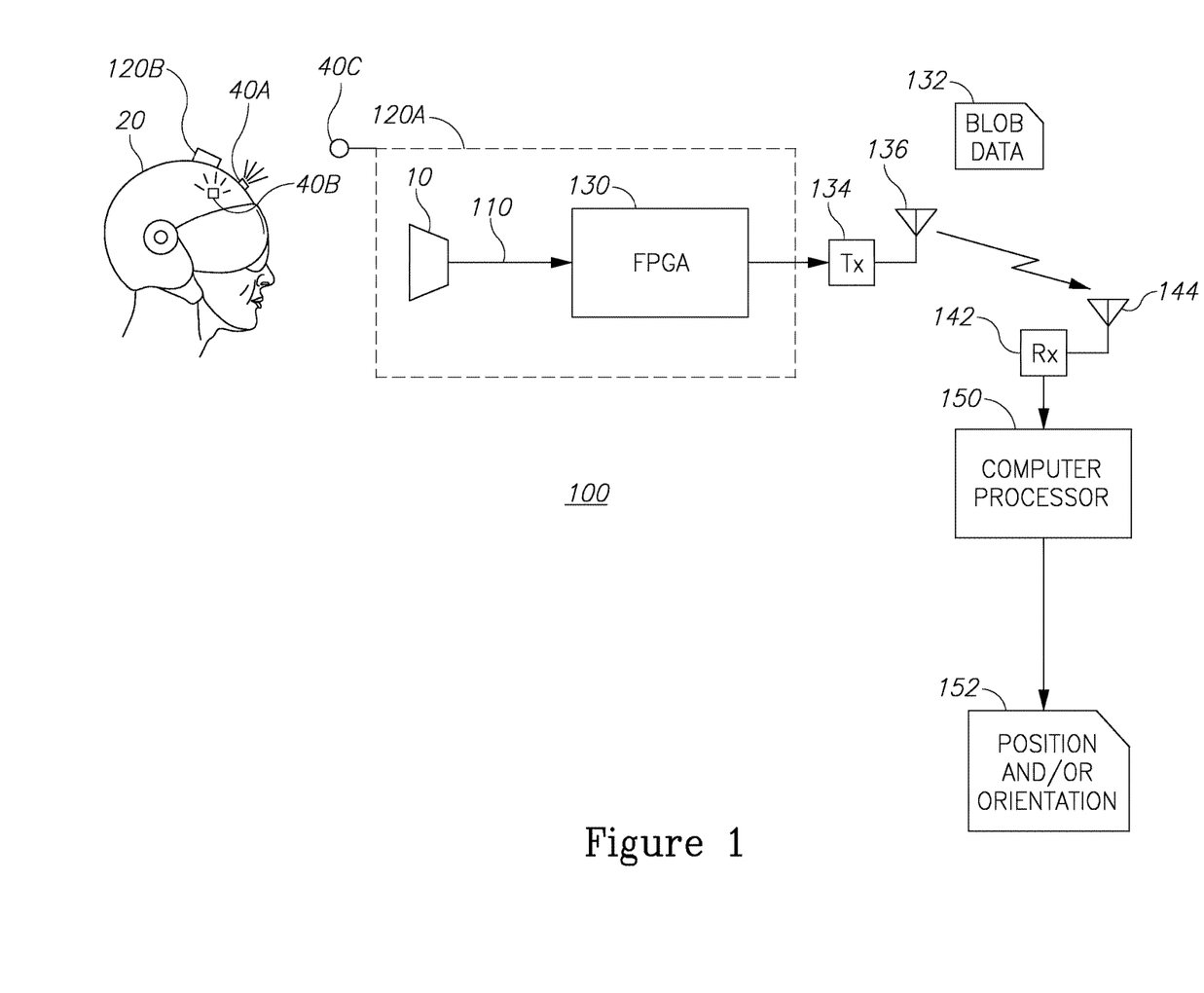
FIG. 1 is a diagram illustrating an aspect of a system according to embodiments of the present invention.

FIG. 1 is a diagram illustrating a system according to embodiments of the present invention. An optical tracker 100 is illustrated and may include: at least two optical tracker sensors such as sensor 120A which includes at least one pixel array sensor 10 configured to generate a stream of pixel values representing a scene containing a plurality of visual indicators such as 40A and 40B affixed to an object 20 (such as a helmet) on which another optical sensor 120B is located facing optical tracker sensor 120A which is also coupled with a visual indicator 40C. Optical tracker sensor 120A may further include an integrated circuit (IC) such as a field programmable gate array (FPGA) 130 which may also be implemented as an application specific integrated circuit (ASIC) physically coupled to said pixel array sensor 10 possibly by interface 110. It is noted that the system may be implemented by any combination of hardware and software as may be suitable and desirable as per the specific application. It is further understood that a single IC may be in communication with a plurality of pixel array sensors and so the single IC may apply the BLOB analysis to data coming from any of the plurality of the pixel array sensors.

In operation, IC 130 may be configured to receive the aforementioned stream of pixel values and apply a single pass binary large object (BLOB) analysis to said stream, to yield BLOB parameters 132 indicative of the at least one visual indicator. Optical tracker 100 may further include a computer processor 150 configured to receive said BLOB parameters 132 optical tracker sensors 120A and 120B and calculate at least one of: a position, an orientation, or partial data thereof 152 of optical tracker sensor 120B relative to said optical tracker sensor 120A. Architecturally, in one embodiment, computer processor 150 may be packed within said optical tracker sensor 120A in order to provide compactness and ease of use.

The aforementioned configuration, namely of two optical tracker sensors 120A and 120B facing each other, at least one visual indicator 40C coupled to one of the optical tracker sensors 120A, and at least two visual indicators 40A and 40A coupled to the other optical tracker sensor 120B, is sufficient for calculating the full six degrees of freedom of the relative position and orientation between the two optical tracker sensors.

A significant advantage of this configuration over currently available optical tracking configurations is that this configuration supports a compact design of at least one of the optical tracker components, namely the optical tracker sensor which is coupled with the single visual indicator. Conversely, in currently available optical tracker configurations, where a single camera faces at least three visual indicators coupled to an object (three visual indicators are the minimal number of visual indicators required for full position and orientation), the distance between any of two visual indicators is required to be greater than a minimal distance which is proportional to the distance between the optical tracker sensor and the tracked object, and further proportional to the required accuracies of the tracker (i.e., better accuracy requires bigger distance). The minimal distance can be reduced if two optical tracker sensors which are separated by yet another minimal distance are used to track the object. In the aforementioned configuration, the single visual indicator and the optical tracker sensor which are coupled to each other can be encapsulated within a compact housing, wherein the size of the housing is almost as small as desired. Namely, the size is limited only by the size of the hardware components it comprises and not by any mathematical or physical limitations that stem from the required accuracies and the distance between this optical tracker component and other components in the system.

The compact design in accordance with embodiments of the present invention is specifically advantageous when the compact component is attached to a hand-held object or to a head-mounted unit as will be detailed below. Other advantages arise from the accuracy and the short and long term mechanical stability of the relative position between the components comprising the optical tracker unit (i.e. the sensor and visual indicator) which itself is required for system accuracy. For example, when the visual indicator is a light emitting diode (LED), such that the LED and the pixel array sensor may both be assembled to a single printed circuit board (PCB), their relative position can be known with the very high accuracies promised by the PCB assembly line. This configuration is also robust to changes due to environmental conditions (e.g. temperature) and mechanical strains. However, generally the wire used to transmit the video from the sensor to the processor is required to support a large bandwidth in order to support a short transmission time of every video frame and thus keep the system latency small. Moreover, sometimes the application requires that no cable is used.

The present invention, in embodiments thereof, addresses the aforementioned challenges of the currently available optical tracker. As explained above, using BLOB analysis reduces the amount of data that need to be transmitted for processing. Yet another embodiment for compact low latency optical tracker may use a video imaging device which is configured to extract pixels only in a predefined region of interest (ROI) instead of the aforementioned BLOB based optical tracker sensor. The video capturing device (which replaces in this embodiment optical sensor 120A and/or 120B) is configured to capture only the ROI which is set to contain the range in which the visual indicators coupled to the other sensor. More variation of the ROI will be explained below. Both BLOB and ROI solutions support a low bandwidth wired or wireless configuration and both embodiments can be used in a single implementation.

Another advantage of the compact design is the possibility to couple several pairs of pixel array sensors and LEDs in a single optical tracker sensor, such that each pair covers a different FOV, and thus a single optical tracker sensor may cover a very large FOV and still remain compact. Only a single pair is required to be employed at any given tracker cycle and therefore the distance between the pairs can be kept minimal.

Determining the BLOB parameters may be achieved by methods of single-pass BLOB analysis known in the art. The single-pass BLOB analysis, as described herein, relates to the ability to scan an entire image and detect all of the objects in the scene and derive their respective BLOB parameters in a single pass of the pixels (as opposed to two and three passes that were required in previous techniques).

In one embodiment of the present invention, a threshold approach is being implemented. Accordingly, each pixel is considered as belonging to a BLOB if its gray-level value is higher than a predetermined threshold. This approach works best in cases where the image contains a relatively small number of BLOBs in a dark background, which is usually the case in optical tracker applications, where various optical and electro-optical means are used in order to render visual indicators more distinguishable over their surroundings.

In one embodiment, the pixels coming from the sensor are read one by one. Once a current pixel is determined as being above a predefined threshold, its BLOB-associated neighboring pixels (e.g., located one or two pixels apart) are also being checked. The current pixel is being associated with the BLOB with which the neighboring pixels are associated. In a case that two neighboring pixels are associated with two different BLOBs, an indication for uniting the two BLOBs is being made. Other manners to implement the BLOB detection are possible. It is understood that other embodiments such as reading the pixels two by two or any other number may also be contemplated.

According to some embodiments of the present invention, computer processor 140 and the at least one optical tracker sensor 120 may be located separately and wherein the optical tracker sensor is further configured to transmit the BLOB parameters 132 via transmitter 134 and antenna 136 to antenna 144 and receiver 142 coupled to computer processor 140. One of the advantages of the present invention is that since the BLOB analysis is carried out in situ (i.e., at the capturing device), the transmitted parameters are not raw data such as video sequence (such as the case with video trackers) and therefore do not require a broad bandwidth. Another advantage of the present invention is that since the BLOB analysis is performed on a single-pass basis and only the BLOB parameter are transmitted, any unnecessary latency between the time when an image is sampled by the pixel array sensor 10 and the time when the computer processer 140 starts its calculation is eliminated.

According to some embodiments of the present invention, where one of the at least two optical tracker sensors is coupled to two visual indicators or more, the second optical tracker sensor facing it only requires a single visual indicator. This requirement stems from the fact that for deriving full relative position and orientation data (i.e., six degrees of freedom) for a pair of optical tracker sensors, at least three visual indicators are required in total.

This configuration may advantageously enable designing a very compact single-visual-indicator optical tracker sensor. The compact optical tracker sensor may be used for coupling to objects to-be-tracked, where small size is an essential advantage such as hand-held devices. The compact optical tracker sensor may include a housing, encapsulating both the single visual indicator and the pixel array sensor. In a non-limiting example, the single visual indicator may be located at a distance less than approximately 5 cm from a center of the pixel array sensor.

According to some embodiments of the present invention, visual indicator 40 may consist of at least one of: a light source, and a reflector or a combination thereof. In addition, the said light source or the light source emitting the light reflected by the reflector may be configured to emit light pulses and wherein the optical tracker further comprising means for synchronization between the pulses of the light source and the integration time of the pixel array sensor 10.

According to some embodiments of the present invention, the stream of pixels is only transferred for at least one predefined region of interest (ROI) within the pixel array sensor 10, where the ROI borders are updated on a frame-by-frame basis. This will further reduce the time elapsed between the capturing of the scene and the completion of the BLOB analysis, since the readout time of the pixels from the sensor 10 will be shorter. This approach works best in cases where the image contains a relatively small number of BLOBs that are restricted to a small part of the image, and their expected position can be roughly predicted based on the past, as is the case when tracking a single object having one or more visual indicators attached to it.

Determining the ROI borders may be carried out based on the predicted locations of the objects to be tracked. Additionally, whenever the sensor technology allows, two or more ROIs may be generated in order to track two or more groups of visual indicators with minimal latency. For example, whenever two objects, each having visual indicators need to be tracked. Alternatively, each object can be independently and separately tracked by synchronizing the periods of time in which the different sensors and light sources are operated.

According to other embodiments, a complementary technology such as magnetic or inertial tracking may be used in case of a temporary loss of optical detection of the visual indicators. Upon resuming of the optical detection, the optical tracker may use the ROI derived from the complimentary tracker (magnetic, inertial, or other). Alternatively, after long periods of loss of optical detection, the optical tracking is resumed in full frame (non-ROI mode).

Figure 2:
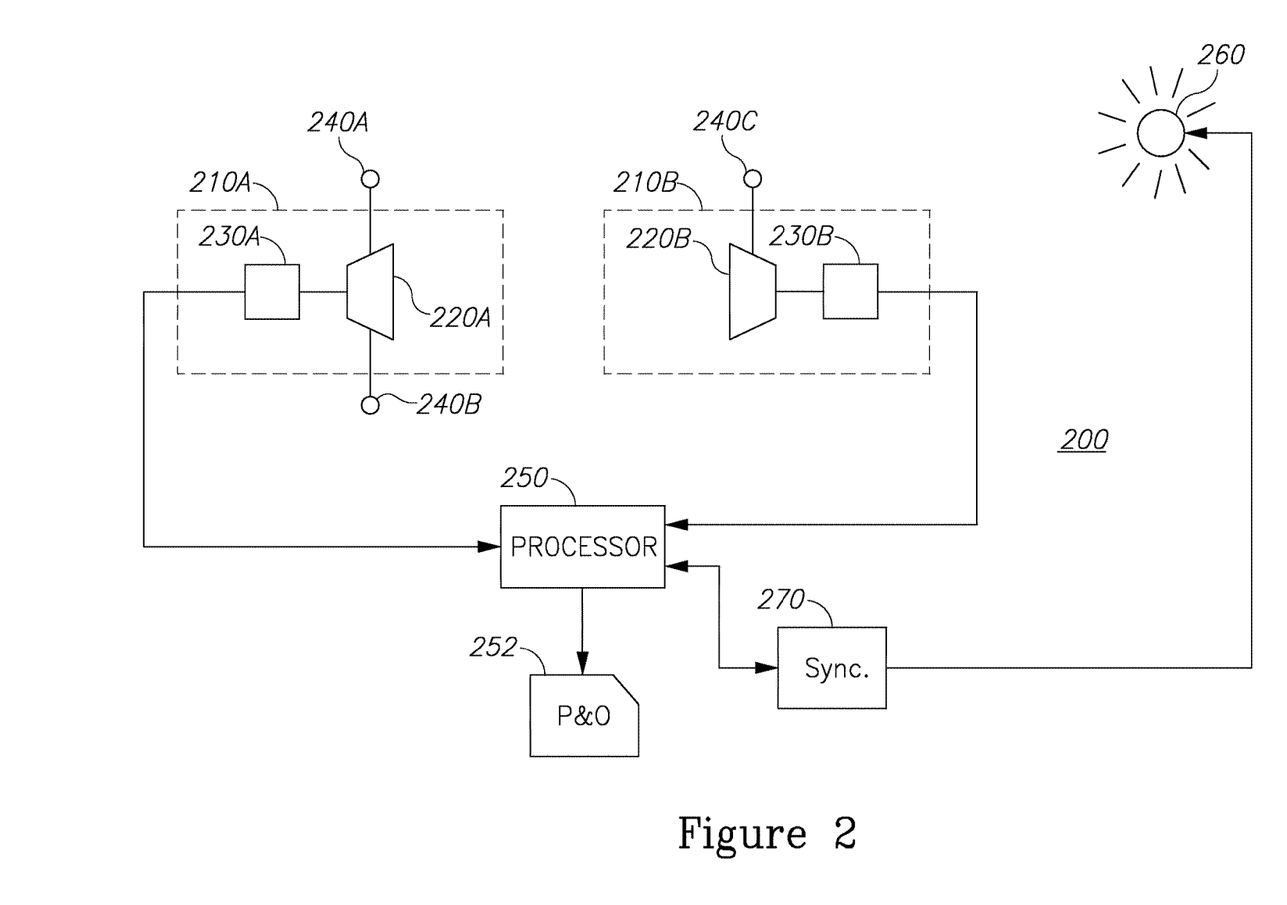
FIG. 2 is a diagram illustrating another aspect of a system according to embodiments of the present invention.

FIG. 2 is a diagram illustrating another aspect of a system according to embodiments of the present invention. Optical tracker 200 may include: at least two optical tracker sensors 210A and 210B facing at least partially each other wherein at least one of said optical tracker sensors includes at least one pixel array sensor 220A and 220B configured to generate a stream of pixel values representing a scene; an integrated circuit (IC) 230A and 230B physically coupled to said at least one pixel array sensor 220A and 220B, and configured to: receive said pixel-by-pixel stream of values; and apply a binary large object (BLOB) analysis to said stream, to yield BLOB parameters indicative of the at least one visual indicator 240A, 240B or 240C present in the scene in a single pass of the pixels representing the scene.

Optical tracker 200 may also include at least one visual indicator 240A, 240B or 240C coupled to each of the at least two optical tracker sensors 210A and 210B. Optical tracker 200 may also include a computer processor 250 configured to receive said BLOB parameters and calculate a relative position and/or orientation 252, or a partial data thereof, of the at least two optical tracker sensors.

According to some embodiments of the present invention, the total number of the visual indicators physically attached to the at least two optical tracker sensors is at least three.

According to some embodiments of the present invention, at least one of the at least two optical tracker sensors is an image capturing device, and wherein the computer processor is configured to calculate the relative position and/or orientation, or a partial data thereof, further based on data derived from the image capturing device.

According to some embodiments of the present invention, at least one of the at least two optical tracker sensors is stationary.

According to some embodiments of the present invention, the computer processor is packed within one of said optical tracker sensors.

According to some embodiments of the present invention, the computer processor and at least one of the optical tracker sensors are located separately from each other and wherein the at least one optical tracker sensor is further configured to transmit the BLOB parameters over a wired communication channel to the computer processor.

According to some embodiments of the present invention, the computer processor and at least one of the optical tracker sensors are located separately from each other and wherein the at least one optical tracker sensor is further configured to transmit the BLOB parameters over a wireless communication channel to the computer processor.

According to some embodiments of the present invention, the at least one visual indicator comprises at least one of: a light source, and a reflector.

According to some embodiments of the present invention, at least one visual indicator is configured to emit or reflect light pulses and wherein the optical tracker further comprises means for synchronization 270 between the light pulses from light source 260 or the visual indicators 240A-C and the at least two optical tracker sensors.

According to some embodiments of the present invention, the optical tracker is operable in a region of interest (ROI) mode in which only a subset of the stream of pixels is transferred to the IC, wherein the subset of stream of pixels represents a predefined subset of the pixel array associated with the ROI.

According to some embodiments of the present invention, the ROI is determined on a frame-by-frame basis based on predicted locations of the at least one visual indicator.

According to some embodiments of the present invention, the optical tracker further comprises magnetic or inertial or other tracking means configured to provide tracking data whenever the optical tracker sensors fail, and wherein the optical tracker is configured to resume optical tracking with an ROI that is determined based on the data provided by the magnetic or inertial or other tracking means.

According to a preferred embodiment of the present invention, the optical tracker comprises two optical tracker sensors and the total number of the visual indicators physically attached to the two optical tracker sensors is at least three. This way, full position and orientation representation may be derived. It is understood however, that using less visual indicators may provide partial position and orientation data that may be beneficial for some applications.

Figure 3:
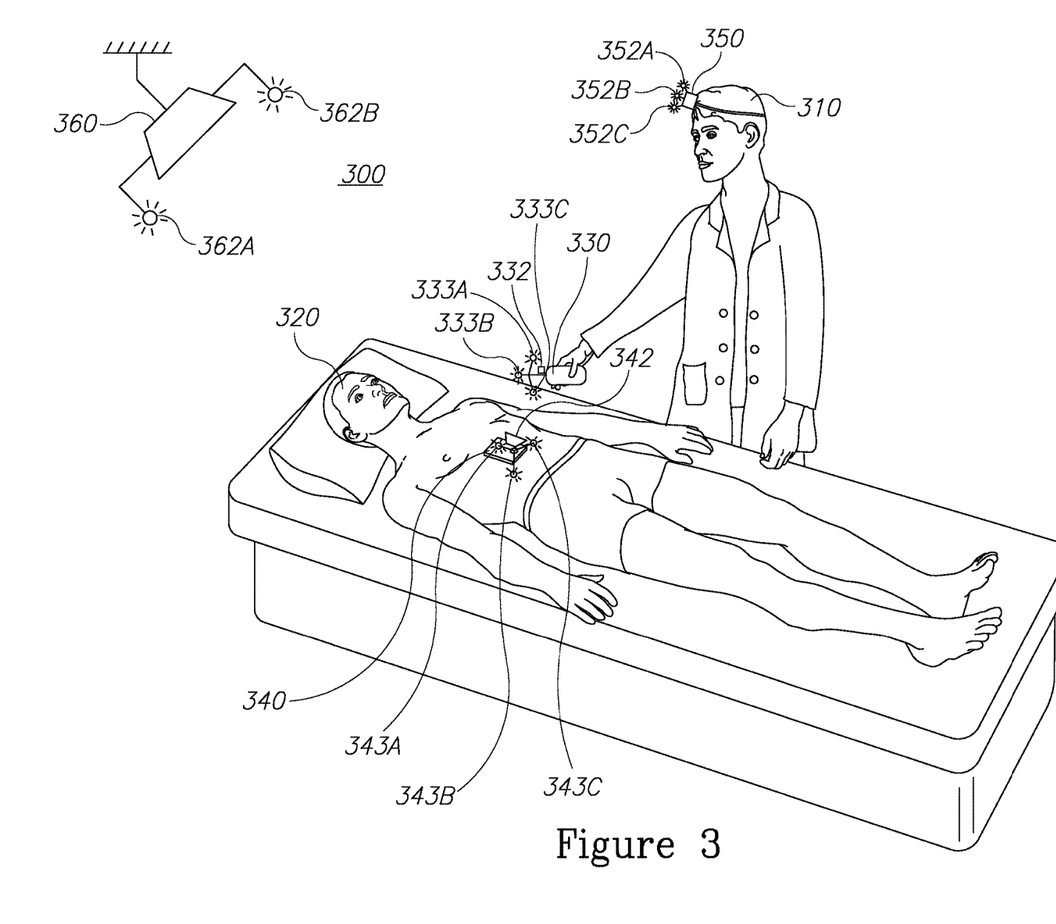
FIG. 3 is a diagram illustrating non-limiting exemplary applications of the system according to embodiments of the present invention.

FIG. 3 is a diagram illustrating non-limiting exemplary applications of the system according to embodiments of the present invention. Environment 300 illustrates an operating room in which a doctor 310 is using a hand held medical device 330 to which the optical sensor 332 and visual indicators 333A, 333B, and 333C are attached. Similarly, optical sensor 350 and visual indicators 353A, 353B, and 353C may be mounted on the head of the doctor 310 possibly with a head mounted display system (not shown). Another optical tracker sensor 360 may be stationary (e.g., attached to the ceiling) and may include at least two visual indicators 362A and 362B. Yet another optical sensor 342 and visual indicators 343A, 343B, and 343C may be patient-mounted to a fixture 340 on a patient 320.

According to some embodiments, the hand-held device 330 may be any operating tool (e.g., a scalpel, a laparoscope tube, an ultrasound transducer or a needle). In this manner, the hand held device may be tracked. It is understood that since the objects to be tracked and the optical tracker sensors coupled thereto define a specific spatial relationship, in order to calculate the relative position and orientation of two objects (as opposed to the relative position and orientation of two optical tracker sensors) in reality, the aforementioned specified spatial relationship needs to be known. There are several ways known in the art for calibration or registration of that spatial relationship.

When the optical tracker sensor 342 is patient-mounted, e.g. physically attached to the patient's head or limb, the fixture 340 on the patient may be tracked. This attachment may be direct or indirect, e.g. the optical tracker sensor may be attached directly to the head of the patient, or may be attached to a frame which is rigidly attached to the head of the patient.

According to some embodiments of the present invention, head-mounted optical sensor or hand-held device optical sensor or patient-mounted optical sensor is located within a field of view of at least one of the at least two optical tracker sensors, and wherein the computer processor is further configured to calculate a position and/or orientation, or a partial data thereof, of the head-mounted optical sensor or hand-held device optical sensor or patient-mounted optical sensor, relative to at least one of the at least two optical tracker sensors.

According to some embodiments of the present invention, at least one of the two optical tracker sensors is patient-mounted or physically attached to a hand-held device and having at least one visual indicator attached thereto, and wherein the head-mounted optical tracker sensor has at least two visual indicators attached thereto.

It is understood that many more combinations and variations of the aforementioned optical sensors and visual indicators may be used, as required per the use or the design of the optical tracking system.

Figure 4:
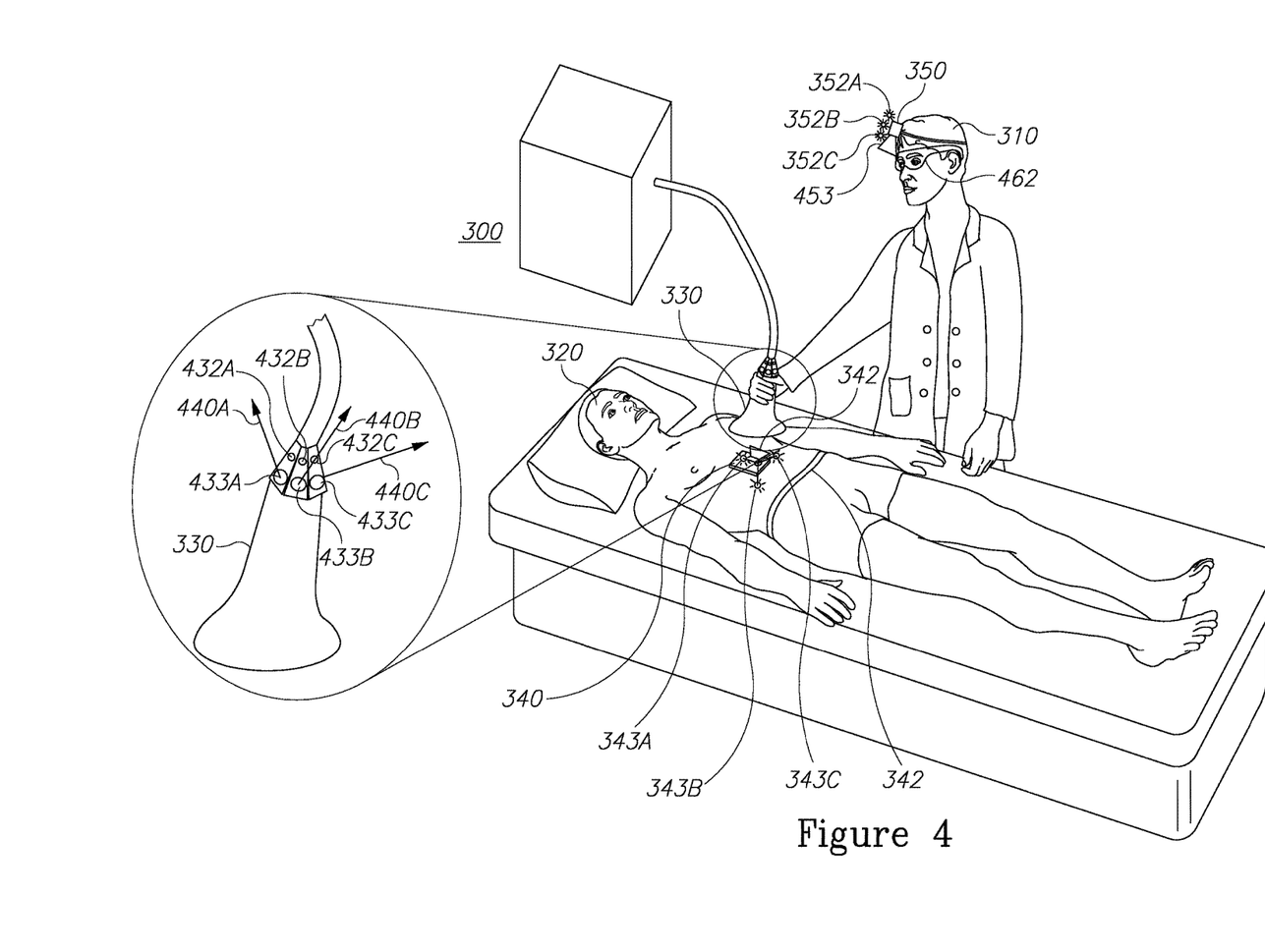
FIG. 4 is a diagram illustrating another non-limiting exemplary application of the system according to embodiments of the present invention.

FIG. 4 is a diagram illustrating yet another non-limiting exemplary application of the system according to embodiments of the present invention. Environment 300 illustrates an operating room in which a human user 310 is donning a head mounted display system which also comprises an optical tracker sensor 453 and at least two visual indicators 352A-352C. Additionally, Human user 310 may be using a hand held medical device 330 to which an optical tracker sensor comprising a plurality of pixel array sensors 433A-433C and a single IC (not shown) is attached. Pixel array sensors 433A-433C are positioned along the perimeter of hand held medical device 330 wherein each one of pixel array sensor 433A-433C is radially facing a different sector which may or may not be adjacently overlapping. Preferably but not exclusively, the pixel array sensors 433A-433C may each be tilted so that the entire structure with the bases of the sensors form a pyramid.

Similarly, corresponding visual indicators such as 432A-432C, preferably light sources such as LEDs are also located along the perimeter of hand held medical device 330 and radially facing different sectors so as to be located in proximity to the respective pixel array sensors 433A-433C. Preferably, but not exclusively, the distance between a pixel array sensor of 433A-433C and its corresponding light source of 432A-432C does not exceed 3 centimeters and the distance between the pixel array sensors 433A-433C does not exceed 5 centimeters. These exemplary limitations enable a compact arrangement of the pixel array sensors and the light sources on a hand held device. The tilt angle provides ergonomic advantages, specifically if the head of the human user 310 is facing down where the hand held device 330 is positioned.

In operation, a dynamic selection of which one of pixel array sensors 433A-433C should be employed in every given tracker cycle is being carried out. Similarly, the corresponding light source (being the one proximal to the pixel array sensor) is also employed. Head mounted optical tracker sensor 453 is constantly capturing one of the light sources 432A-432C which are being selectively operated based on the spatial angle of the hand held device. In the same time only one of pixel array sensor 433A-433C whose field of view (FOV) includes the visual indicators 352A-352C of the head mounted device 350 is being employed at a given cycle.

The aforementioned design combines the benefits of robust tracking with compactness of the tracker. The logic enables a more robust tracking as the hand held device is not limited by a narrow field of view of a single optical sensor. The aforementioned structure provides compactness which is specifically advantageous where the optical sensors need to be attached to a hand held device where compactness is crucial.

Figure 5A:
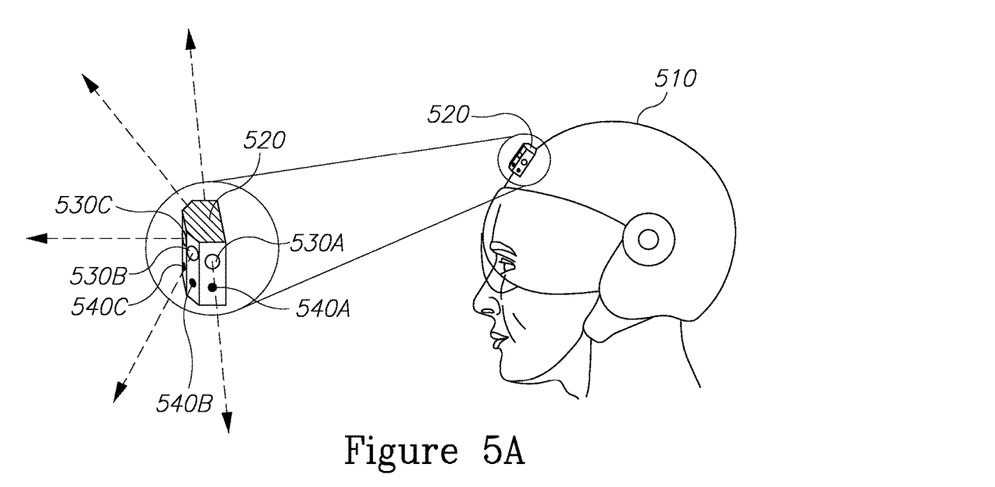
FIGS. 5A and 5B are diagrams illustrating further non-limiting exemplary applications of the system according to embodiments of the present invention.

FIG. 5A shows yet another embodiment according to the present invention. In FIG. 5A, an optical tracker sensor 520 which comprises pixel array sensors 530A-530C and their corresponding LEDs 540A-540C is attached to a pilot helmet 510, where the pilot is sitting in a cockpit facing an optical tracker sensor coupled with at least two visual indicators and affixed to the cockpit as a frame of reference (not shown). Advantageously, the helmet user is not limited ergonomically in its head orientation for a good operation of the tracker. This is achieved due to the wide field of view of the on-helmet optical tracker sensor 520.

Figure 5B:
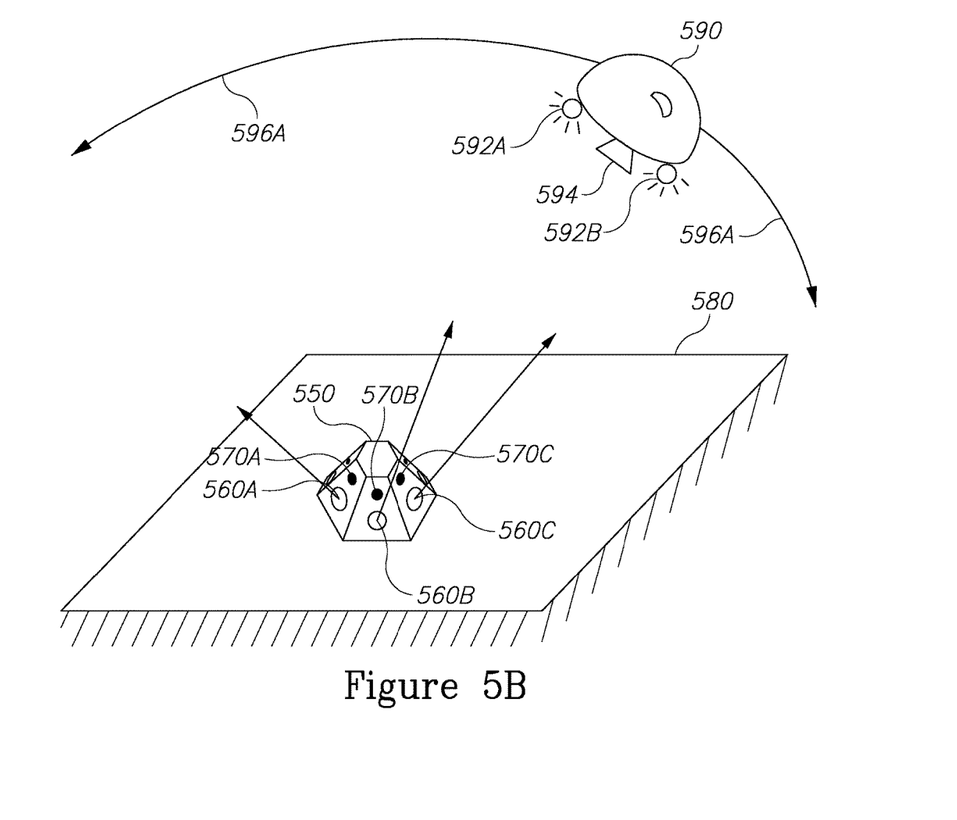

FIG. 5B illustrates a stationary optical tracker unit 550 comprising pixel array sensors 560A-560C and their corresponding LEDs 570A-570C, which are located along different surfaces of optical tracker unit 550, each with a different radial angle with an additional tilt. A second optical tracking unit 590 which includes two LEDS 562A and 592B and an optical tracker sensor 494 are provided with better freedom of orientation and position (illustrated by arrows 596A and 596B) in the scene without losing tracking capabilities, due to the wider field of view of stationary tracking unit 550. This configuration can be advantageous for instance when the stationary unit is attached to a patient and the moving unit is attached to a head mounted display system donned by a physician. In this situation the optical tracker keeps tracking the relative position and orientation between the head mounted system and the patient while the physician walks around the patient.

As will be appreciated by one skilled in the art, aspects of the present invention may be embodied as a system, method or an apparatus. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The aforementioned flowchart and block diagrams illustrate the architecture, functionality, and operation of possible implementations of systems and methods according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions. It will further be recognized that the aspects of the invention described hereinabove may be combined or otherwise coexist in embodiments of the invention.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention.

The invention claimed is:

1. An optical tracker comprising:
   at least two optical tracker sensors, facing at least partially each other, wherein at least one of said optical tracker sensors comprises:
   at least one pixel array sensor configured to generate a stream of pixel values representing a scene;
   an integrated circuit (IC) physically coupled to said at least one pixel array sensor, and configured to:
   (a) receive said stream of pixel values;
   (b) apply a binary large object (BLOB) analysis to said stream, to yield BLOB parameters indicative of the at least one visual indicator present in the scene in a single pass of the pixels representing the scene;
   at least one visual indicator coupled to each of the at least two optical tracker sensors; and
   a computer processor configured to receive said BLOB parameters and calculate a relative position and/or orientation, or a partial data thereof, of the at least two optical tracker sensors,
   wherein each of the visual indicators coupled to a respective optical tracker sensor is located at a distance of less than 10 cm from a center of any of the pixel array sensors of the corresponding optical tracker sensor.

2. The optical tracker according to claim 1, wherein the total number of the visual indicators physically attached to the at least two optical tracker sensors is at least three for each pair of optical tracker sensors for which the position and orientation is calculated in full.

3. The optical tracker according to claim 1, wherein at least one of the at least two optical tracker sensors is an image capturing device, and wherein the computer processor is configured to calculate the relative position and/or orientation, or a partial data thereof, further based on data derived from the image capturing device.

4. The optical tracker according to claim 1, wherein at least one of the at least two optical tracker sensors is stationary.

5. The optical tracker according to claim 1, wherein at least one of the at least two optical tracker sensors is head-mounted.

6. The optical tracker according to claim 1, wherein at least one of the at least two optical tracker sensors is physically attached to a hand-held device.

7. The optical tracker according to claim 1, wherein at least one of the at least two optical tracker sensors is patient-mounted or rigidly attached to a patient.

8. The optical tracker according to claim 1, wherein said head-mounted optical sensor or hand-held device optical sensor or patient-mounted optical sensor is located within a field of view of at least one of the at least two optical tracker sensors, and wherein the computer processor is further configured to calculate a position and/or orientation, or a partial data thereof, of the head-mounted optical sensor or hand-held device optical sensor or patient-mounted optical sensor, relative to at least one of the at least two optical tracker sensors.

9. The optical tracker according to claim 5, wherein at least one of the two optical tracker sensors is patient-mounted or physically attached to a hand-held device and having at least one visual indicator attached thereto, and wherein the head-mounted optical tracker sensor has at least two visual indicators attached thereto.

10. The optical tracker according to claim 4, wherein at least one of the two optical tracker sensors is patient-mounted or physically attached to a hand-held device and having at least one indicator attached thereto, and wherein the stationary optical tracker sensor has at least two visual indicators attached thereto.

11. The optical tracker according to claim 1, wherein said computer processor is packed within one of said optical tracker sensors.

12. The optical tracker according to claim 1, wherein the computer processor and at least one of the optical tracker sensors are located separately from each other and wherein the at least one optical tracker sensor is further configured to transmit the BLOB parameters over a wired communication channel to the computer processor.

13. The optical tracker according to claim 1, wherein the computer processor and at least one of the optical tracker sensors are located separately from each other and wherein the at least one optical tracker sensor is further configured to transmit the BLOB parameters over a wireless communication channel to the computer processor.

14. The optical tracker according to claim 1, wherein the at least one visual indicator comprises at least one of: a light source, and a reflector.

15. The optical tracker according to claim 1, wherein the at least one visual indicator is configured to emit or reflect light pulses and wherein the optical tracker further comprises means for synchronization between the light pulses and the at least two optical tracker sensors.

16. The optical tracker according to claim 1, operable in a region of interest (ROI) mode in which only a subset of the stream of pixels is transferred to the IC, wherein the subset of steam of pixels represents a predefined subset of the pixel array associated with the ROI.

17. The optical tracker according to claim 16, wherein the ROI is determined on a frame-by-frame basis based on predicted locations of the at least one visual indicator.

18. The optical tracker according to claim 16, further comprising magnetic or inertial or other tracking means configured to provide tracking data whenever the optical tracker sensors fail, and wherein the optical tracker is configured to resume optical tracking with an ROI that is determined based on the data provided by the magnetic or inertial or other tracking means.

19. The optical tracker according to claim 1, further comprising a housing, wherein at least one optical tracker sensor is coupled to a single visual indicator which is located at a distance less than 10 cm from a center of the pixel sensor array, wherein said single visual indicator and said pixel sensor array are packed within said housing.

* * * * *